United States Patent
Beckman et al.

(10) Patent No.: US 11,045,745 B2
(45) Date of Patent: Jun. 29, 2021

(54) REACTIVE EXTRACTION OF WATER

(71) Applicant: University of Pittsburgh—Of the Commonwealth System of Higher Education, Pittsburgh, PA (US)

(72) Inventors: Eric J. Beckman, Aspinwall, PA (US); Ioannis Bourmpakis, Wexford, PA (US); Nathan Albert Tavenor, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 16/493,745

(22) PCT Filed: Mar. 13, 2018

(86) PCT No.: PCT/US2018/022137
§ 371 (c)(1),
(2) Date: Sep. 12, 2019

(87) PCT Pub. No.: WO2018/169928
PCT Pub. Date: Sep. 20, 2018

(65) Prior Publication Data
US 2020/0078703 A1 Mar. 12, 2020

Related U.S. Application Data

(60) Provisional application No. 62/470,664, filed on Mar. 13, 2017.

(51) Int. Cl.
*B01D 11/04* (2006.01)
*C02F 1/26* (2006.01)
(Continued)

(52) U.S. Cl.
CPC .......... *B01D 11/0492* (2013.01); *C01B 5/00* (2013.01); *C02F 1/265* (2013.01); *C07C 17/38* (2013.01); *C02F 2303/18* (2013.01)

(58) Field of Classification Search
CPC .... B01D 11/04; B01D 11/0492; B01D 17/00; C02F 1/265; C02F 2303/18; C02F 1/02;
(Continued)

(56) References Cited

U.S. PATENT DOCUMENTS 3,155,610 A * 11/1964 Williams .................. C02F 1/26
210/710
3,217,505 A 11/1965 Tuwiner
(Continued)

FOREIGN PATENT DOCUMENTS

GB 388553 A 3/1933

OTHER PUBLICATIONS

J. Peter Guthrie, "Hydration of Carbonyl Compounds, an Analysis in Terms of Multidimensional Marcus Theory", Published in Journal of American Chemical Society, 2000, vol. 122, pp. 5529-5538. (Year: 2000).*

(Continued)

*Primary Examiner* — Joseph W Drodge
(74) *Attorney, Agent, or Firm* — Foley & Lardner LLP

(57) ABSTRACT

Described herein are methods and compounds for extracting water from an aqueous solution. For example, some embodiments include method for extracting water from an aqueous solution, comprising contacting the aqueous solution with a compound comprising one or more carbonyl moieties having an equilibrium constant for a hydration of the carbonyl moiety of at least about 0.5; separating a composition comprising the hydrated compound from the aqueous solution; and reacting the hydrated compound to obtain water.

19 Claims, 3 Drawing Sheets

(51) Int. Cl.
*C07C 17/38* (2006.01)
*C01B 5/00* (2006.01)

(58) Field of Classification Search
CPC ...... C02F 1/04; C02F 1/26; C02F 1/68; C02F 2103/08; C02F 2305/00; C02F 2305/14; C07C 17/38; C01B 5/00; A23L 2/00
USPC .... 210/634, 638, 639, 749, 774; 203/10, 28, 203/29, 38; 423/416, 580.1; 426/66
See application file for complete search history.

(56) References Cited

U.S. PATENT DOCUMENTS

| | | | | |
|---|---|---|---|---|
| 3,234,125 | A * | 2/1966 | Bloch | C02F 1/26 210/633 |
| 3,856,492 | A * | 12/1974 | Klass | C02F 1/22 62/533 |
| 4,360,434 | A * | 11/1982 | Kawaguchi | B01D 67/0093 210/500.28 |
| 4,678,583 | A * | 7/1987 | Willson, III | B01D 11/0492 210/638 |
| 6,890,444 | B1 * | 5/2005 | Max | C02F 1/26 210/737 |
| 9,428,404 | B2 | 8/2016 | Bajpayee et al. | |
| 2007/0108131 | A1 * | 5/2007 | Skjetne | C02F 1/26 210/714 |
| 2014/0263050 | A1 | 9/2014 | Sowa, Jr. et al. | |

OTHER PUBLICATIONS

International Search Report issued in International Patent Application No. PCT/US2018/022137, dated Jul. 12, 2018.
Bushman et al., "The Reversible Hydration of Carbonyl Compounds in Aqueous Solution. Part I, The Keto/Gem-diol Equilibrium," Reports of the Bunsen Society for Physical Chemistry, vol. 84, No. 1, pp. 41-44 (1980).
Davis, et al., "Synthesis of α-Fluoro Aldehydes and Ketones. A Review," *Org. Prep. and Proc. Intern.*, vol. 31, No. 2, pp. 125-143 (1999).
Greenzaid et al., "A Nuclear Magnetic Resonance Study of the Reversible Hydration of Aliphatic Aldehydes and Ketones. I. Oxygen-17 and Proton Spectra and Equilibrium Constants." *J. Amer. Chem. Soc.* 89: 749-756 (1967).
Kosobokov et al., "Difluorohomologation of Ketones," *Org. Lett.*, 17:760-763 (2015).
R. Gomez-Bombarelli et al., "Computational Calculation of Equilibrium Constants: Addition to Carbonyl Compounds," *J. Phys. Chem. A.*, vol. 113, pp. 11423-11428 (2009).
R. Stewart, et al., "The Hydration of Ketones in Mixtures of Water and Polar Aprotic Solvents," *Can. J. Chem.*, vol. 50, pp. 1992-1999 (1972).
Wiberg et al., "Thermochemistry of Carbonyl Reactions. 6. A Study of Hydration Equilibria," J. Am. Chem. Soc., 116:11067-11077 (1994).
Y. Zhao, et al., " The M06 suite of density functionals for main group thermochemistry, thermochemical kinetics, noncovalent interactions, excited states, and transition elements: two new functionals and systematic testing of four M06-class functionals and 12 other functionals," *Theor. Chem. Acc.*, vol. 120, pp. 215-241 (2008).
Zhang et al., "Copper-Assisted Direct Nitration of Cyclic Ketones with Ceric Ammonium Nitrate for the Synthesis of Tertiary α-Nitro-α-substituted Scaffolds," Org. Lett. 19: pp. 1124-1127 (2017).
Zuend et al., "A thermodynamic model of mixed organic-inorganic aerosols to predict activity coefficients," *Atmos. Chem. Phys.*, vol. 8, pp. 6069-6151 (2008).
Zuend et al., "New and extended parameterization of the thermodynamic model AIOMFAC: calculation of activity coefficients for organic-inorganic mixtures containing carboxyl, hydroxyl, carbonyl, ether, ester, alkenyl, alkyl, and aromatic functional groups," *Atmos. Chem. Phys.*, vol. 11, pp. 9155-9206 (2011).
International Preliminary Report on Patentability issued in International Patent Application No. PCT/US2018/022137, dated Sep. 26, 2019.

* cited by examiner

REACTIVE EXTRACTION OF WATER

CROSS-REFERENCE TO RELATED APPLICATIONS

Osmosis This application claims priority to U.S. Provisional Patent Application No. 62/470,664 filed Mar. 13, 2017, which is incorporated herein by reference in its entirety.

BACKGROUND

Osmosis is the thermodynamic driving force that drives solvent to dilute more concentrated solutions. For example, osmosis drives water to mix with, and hence dilute, salt. To generate potable water from saline mixtures, efforts have been undertaken to perform the opposite process—overcoming osmosis and thus separating water from mixtures with salt. Conventional technologies that separate water from brine counteract osmotic driving force by, e.g., application of very high pressure across a semi-permeable membrane (reverse osmosis, "RO"), application of an even higher osmotic pressure across a membrane (forward osmosis, "FO") followed by thermal separation, and simply application of significant thermal energy (distillation). Because osmotic pressure increases nonlinearly with salt concentration, RO and FO processes produce concentrated brine byproducts—one that ultimately reaches the point where sufficient pressure to move water through the membrane cannot be achieved. As such, concentrated salt solutions cannot be purified by RO or FO, leaving only energy-intensive distillation as a remedy.

Ketones are functional groups capable of undergoing hydration to form gem diols. This reversible hydration of ketones has been generally known for well over 50 years [e.g., Wiberg et al., *J. Am. Chem. Soc.*, 116:11067-11077 (1994); R. Stewart and J. D. Van Dyke, *Can. J. Chem.*, 50:1992-1999 (1972)]. Chemists have conducted a number of fundamental investigations into the impact of chemical structure on hydration equilibrium [R. Gomez-Bombarelli et al., *J. Phys. Chem. A.*, 113:11423-11428 (2009)], in particular examining the impact on the equilibrium constant of the groups appended to the gem diol carbon.

A need exists in the art to find solutions for purifying water that are, e.g., less energy intensive and/or that are capable of producing purified water at a reduced cost or greater scale.

SUMMARY

The present disclosure include methods and compounds for extracting water from an aqueous solution.

An aspect of the disclosure includes a method for extracting water from an aqueous solution, comprising: (a) contacting the aqueous solution with a compound comprising one or more carbonyl moieties having an equilibrium constant for a hydration of the carbonyl moiety of at least about 0.5; (b) separating a composition comprising the hydrated compound from the aqueous solution; and (c) reacting the hydrated compound to obtain water. In some embodiments, the aqueous solution comprises a salt. In some embodiments, the aqueous solution is brine. In some embodiments, the compound comprising one or more carbonyl moieties comprises one or more electron withdrawing moieties alpha to the carbonyl. In some embodiments, the compound comprising one or more carbonyl moieties comprises two or more electron withdrawing moieties alpha or beta to the carbonyl. In some embodiments, the electron withdrawing moiety is independently in each instance selected from the group consisting of —Z or

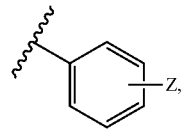

and wherein Z is selected from —F, —Cl, —CN, NO$_2$, carbonyl, and —COO-alkyl. In some embodiments, the compound comprising one or more carbonyl moieties has a boiling point of greater than about 100° C. In some embodiments, reacting the hydrated compound to obtain water comprises heating the hydrated compound to a temperature of about 40° C. to about 100° C. In some embodiments, the compound comprising one or more carbonyl moieties has a molecular weight of about 150 g/mol to about 700 g/mol. In some embodiments, the compound comprising one or more carbonyl moieties is chemically attached to crosslinked beads or thin films. In some embodiments, the compound comprising one or more carbonyl moieties is represented by formula (I):

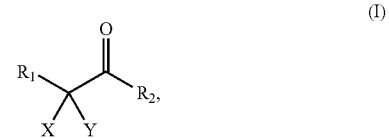

wherein: X is an electron withdrawing moiety; Y is selected from the group consisting of an electron withdrawing moiety, H, optionally substituted alkyl, alkenyl, alkynyl, alkoxy, alkenoxy, alkynoxy, aryloxy, aralkyloxy, heterocyclyloxy, heterocyclylalkoxy, heteroalkyl, heteroalkenyl, heteroalkynyl, and siloxanes, or X and Y of formula (I) together form a carbonyl or thioketone moiety; R$_1$ is selected from the group consisting of optionally substituted alkyl, alkenyl, alkynyl, alkoxy, alkenoxy, alkynoxy, aryloxy, aralkyloxy, heterocyclyloxy, heterocyclylalkoxy, heteroalkyl, heteroalkenyl, heteroalkynyl, and siloxanes; R$_2$ is selected from the group consisting of H, optionally substituted alkyl, alkenyl, alkynyl, alkoxy, alkenoxy, alkynoxy, aryloxy, aralkyloxy, heterocyclyloxy, heterocyclylalkoxy, heteroalkyl, heteroalkenyl, heteroalkynyl, and siloxanes; with the proviso that when Y is H, then at least one of R$_1$ or R$_2$ is

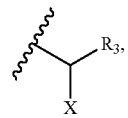

wherein R$_3$ is selected from the group consisting of optionally substituted alkyl, alkenyl, alkynyl, alkoxy, alkenoxy, alkynoxy, aryloxy, aralkyloxy, heterocyclyloxy, heterocyclylalkoxy, heteroalkyl, heteroalkenyl, heteroalkynyl, and siloxanes. In some embodiments, the compound of formula (I) has a molecular weight of at least about 150 g/mol. In some embodiments, the electron withdrawing moiety is independently in each instance selected from the group consisting of —Z or

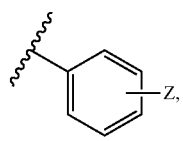

wherein Z is selected from —F, —Cl, —Br, —CF$_3$, —CF$_2$H, —CFH$_2$, —CN, NO$_2$, and —COO-alkyl. In some embodiments, the compound has a theoretical equilibrium constant for a hydration of the carbonyl moiety of at least about 1 as calculated by first principles to calculate Gibbs free energy change of a reaction ($\Delta G$) and then calculate the equilibrium constant of a reaction as $K_{eg}=e^{-\Delta G/RT}$ using the M06-2X level of theory. In some embodiments, the electron withdrawing moiety is —Z, wherein Z is selected from —F, —Cl, —Br, —CF$_3$, —CF$_2$H, —CFH$_2$, —CN, NO$_2$, and —COO-alkyl. In some embodiments, the compound has an equilibrium constant for a hydration of the carbonyl moiety of at least about 1. In some embodiments, Y is H. In some embodiments, R$_1$ is represented by (A). In some embodiments, R$_2$ is represented by (A). In some embodiments, the method is conducted on at least a 100 L scale.

Other aspects of the disclosure include, a compound represented by formula (I):

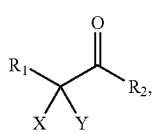

(I)

wherein: X is an electron withdrawing moiety; Y is selected from the group consisting of an electron withdrawing moiety, H, optionally substituted alkyl, alkenyl, alkynyl, alkoxy, alkenoxy, alkynoxy, aryloxy, aralkyloxy, heterocyclyloxy, heterocyclylalkoxy, heteroalkyl, heteroalkenyl, heteroalkynyl, and siloxanes, or X and Y of formula (I) together form a carbonyl or thioketone moiety; R$_1$ is selected from the group consisting of optionally substituted alkyl, alkenyl, alkynyl, alkoxy, alkenoxy, alkynoxy, aryloxy, aralkyloxy, heterocyclyloxy, heterocyclylalkoxy, heteroalkyl, heteroalkenyl, heteroalkynyl, and siloxanes; R$_2$ is selected from the group consisting of H, optionally substituted alkyl, alkenyl, alkynyl, alkoxy, alkenoxy, alkynoxy, aryloxy, aralkyloxy, heterocyclyloxy, heterocyclylalkoxy, heteroalkyl, heteroalkenyl, heteroalkynyl, and siloxanes; with the proviso that when Y is H, then at least one of R$_1$ or R$_2$ is represented by (A)

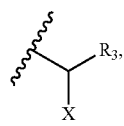

(A)

wherein R$_3$ is selected from the group consisting of optionally substituted alkyl, alkenyl, alkynyl, alkoxy, alkenoxy, alkynoxy, aryloxy, aralkyloxy, heterocyclyloxy, heterocyclylalkoxy, heteroalkyl, heteroalkenyl, heteroalkynyl, and siloxanes. In some embodiments, the compound of formula (I) has a molecular weight of at least about 150 g/mol. In some embodiments, the electron withdrawing moiety is independently in each instance selected from the group consisting of —Z or

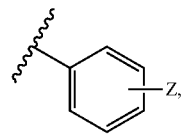

wherein Z is selected from —F, —Cl, —Br, —CF$_3$, —CF$_2$H, —CFH$_2$, —CN, NO$_2$, and —COO-alkyl. In some embodiments, the compound has an equilibrium constant for a hydration of the carbonyl moiety of at least about 1. In some embodiments, Y is H. In some embodiments, R$_1$ is represented by (A). In some embodiments, R$_2$ is represented by (A). In some embodiments, Y is the electron withdrawing moiety. In some embodiments, each of R$_1$ and R$_2$ is an optionally substituted alkyl. Some embodiments include a composition comprising 100 L or more of the compound of the previous embodiments.

Other aspects of the disclosure include, a compound represented by formula (II):

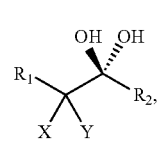

(II)

wherein: X is an electron withdrawing moiety; Y is selected from the group consisting of an electron withdrawing moiety, H, optionally substituted alkyl, alkenyl, alkynyl, alkoxy, alkenoxy, alkynoxy, aryloxy, aralkyloxy, heterocyclyloxy, heterocyclylalkoxy, heteroalkyl, heteroalkenyl, and siloxanes, or X and Y of formula (II) together form a carbonyl or thioketone moiety; R$_1$ is selected from the group consisting of optionally substituted alkyl, alkenyl, alkynyl, alkoxy, alkenoxy, alkynoxy, aryloxy, aralkyloxy, heterocyclyloxy, heterocyclylalkoxy, heteroalkyl, heteroalkenyl, heteroalkynyl, and siloxanes; R$_2$ is selected from the group consisting of H, optionally substituted alkyl, alkenyl, alkynyl, alkoxy, alkenoxy, alkynoxy, aryloxy, aralkyloxy, heterocyclyloxy, heterocyclylalkoxy, heteroalkyl, heteroalkenyl, heteroalkynyl, and siloxanes; with the proviso that when Y is H, then at least one of R$_1$ or R$_2$ is

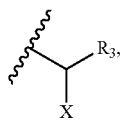

wherein R$_3$ is selected from the group consisting of optionally substituted alkyl, alkenyl, alkynyl, alkoxy, alkenoxy, alkynoxy, aryloxy, aralkyloxy, heterocyclyloxy, heterocyclylalkoxy, heteroalkyl, heteroalkenyl, heteroalkynyl, and siloxanes. In some embodiments, the compound of formula (II) has a molecular weight of at least about 150 g/mol. In some embodiments, the electron withdrawing moiety is independently in each instance selected from the group consisting of —Z or

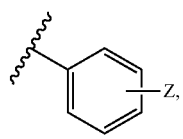

wherein Z is selected from —F, —Cl, —Br, —CF$_3$, —CF$_2$H, —CFH$_2$, —CN, NO$_2$, and —COO-alkyl. In some embodiments, Y is H. In some embodiments, R$_1$ is represented by (A). In some embodiments, R$_2$ is represented by (A). In some embodiments, Y is the electron withdrawing moiety. In some embodiments, each of R$_1$ and R$_2$ is an optionally substituted alkyl. Some embodiments include a composition comprising 100 L or more of the compound of the previous embodiments.

The foregoing general description and following brief description of the drawings and detailed description are exemplary and explanatory and not limiting of the disclosure.

DETAILED DESCRIPTION

I. Method of Extracting Water

Figure 1:
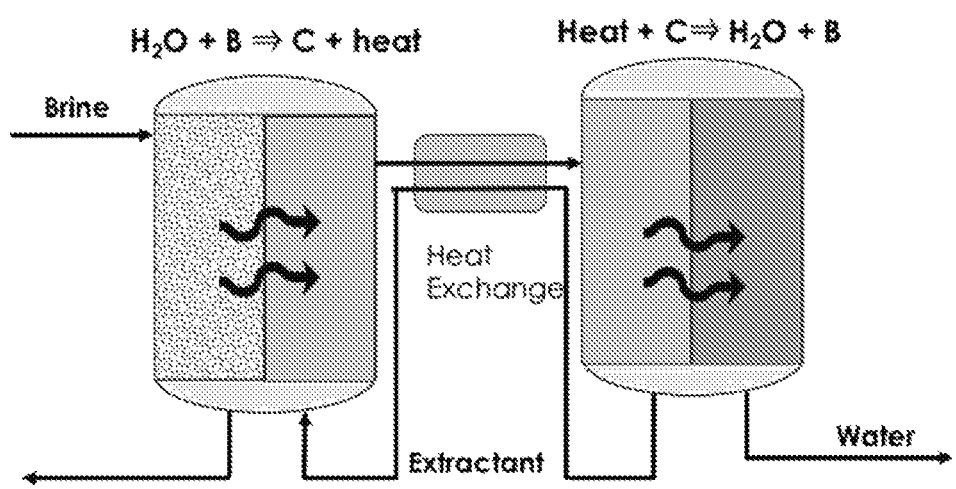
FIG. 1 shows an embodiment of the process configuration for the disclosed subject matter.
Figure 2:
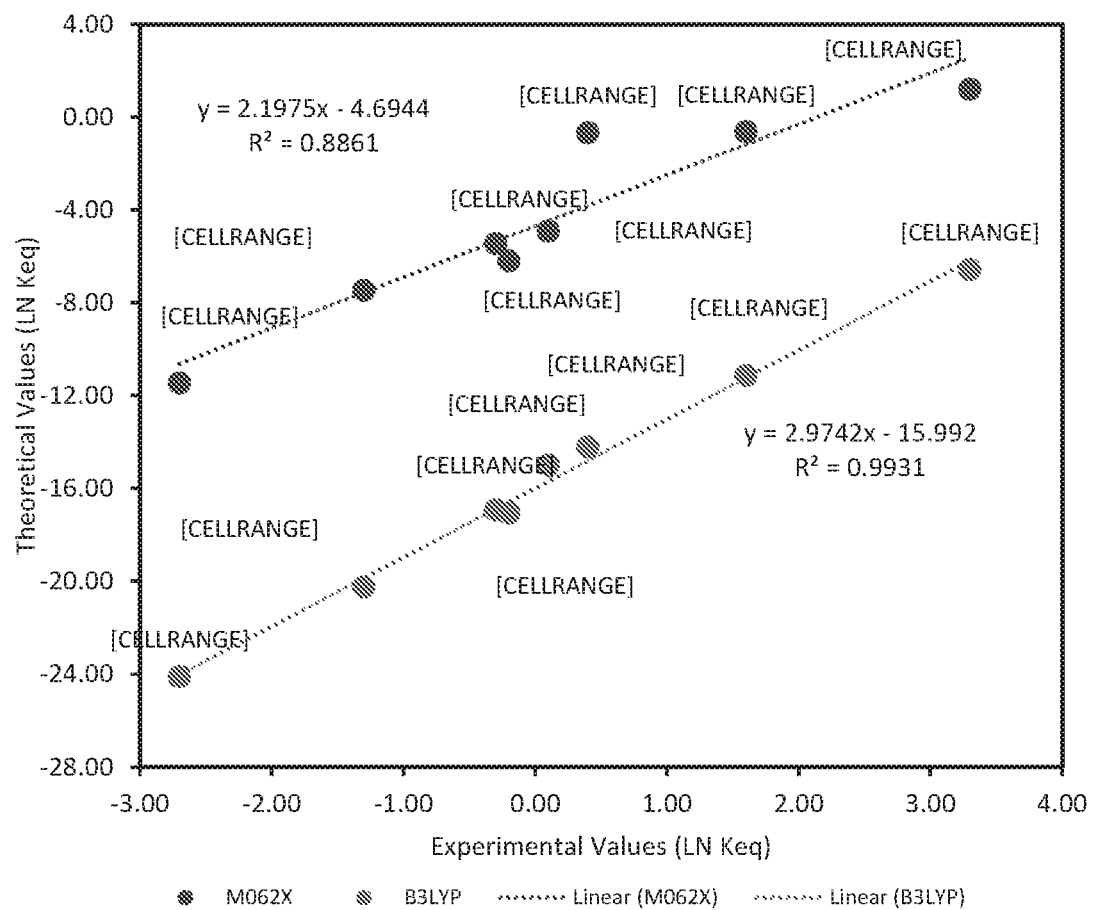
FIG. 2 shows density functional theory results; calculated equilibrium constants for hydration of carbonyls versus literature values.

The present disclosure relates, in some embodiments, to methods for extracting water from an aqueous solution. For example, some embodiments include a method for extracting water from an aqueous solution, comprising (a) contacting the aqueous solution with a compound comprising one or more carbonyl moieties having an equilibrium constant for a hydration of the carbonyl moiety of at least about 0.5; (b) separating a composition comprising the hydrated compound from the aqueous solution; and (c) reacting the hydrated compound to obtain water.

The aqueous solution comprises one or more impurities. For example, the aqueous solution may comprise a salt, such as a non-metallic salt like sodium, potassium, etc. In some embodiments, the concentration of the impurity (e.g., salt) is 1, 2, 3, 4, 5, 6, 7, 8, 9, 10, 11, 12, 13, 14, or 15 wt. %. In some embodiments, the aqueous solution may be brine or seawater. In other embodiments, the aqueous solution may comprise protenaceous material, such as protein molecules, or another material that is difficult to dehydrate.

The compound comprising one or more carbonyl moieties of the method has an equilibrium constant for a hydration of the carbonyl moiety of at least about 0.5. In some embodiments, the equilibrium constant for hydration of the carbonyl moiety is about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0. In some embodiments, the equilibrium constant for hydration of the carbonyl moiety is within a range of two of the preceding values. In other embodiments, the equilibrium constant for hydration of the carbonyl moiety is greater than at least one of the preceding values.

The equilibrium constant for hydration of the carbonyl moiety may be determined experimentally. In other embodiments, the equilibrium constant for hydration of the carbonyl moiety may be theoretical, determined by first principles calculations, such as density functional theory calculations, using state of the art functionals, such as the M06-2X [see, e.g., Y. Zhao, et al., *Theor. Chem. Acc.*, 120:215-241 (2008)] to determine the equilibrium constant through calculating the free energy of reactions.

In some embodiments, the compound comprising one or more carbonyl moieties may be defined by a functional characteristic, such as boiling point or molecular weight. For example, in some embodiments, the compound comprising one or more carbonyl moieties has a boiling point of greater than 100° C. For example, the compound may have a boiling point of greater than about 100° C.; about 110° C.; about 120° C.; about 130° C.; about 140° C.; about 150° C.; about 160° C.; about 170° C.; about 180° C.; about 190° C.; about 200° C.; about 210° C.; about 220° C.; about 230° C.; about 240° C.; about 250° C.; about 260° C.; about 270° C.; about 280° C.; or about 290° C. In some embodiments, the boiling point is within a range of two of the preceding values. Other exemplary embodiments include where the compound comprising one or more carbonyl moieties has a molecular weight of at least about 150 g/mol; about 200 g/mol; about 250 g/mol; about 300 g/mol; about 350 g/mol; about 400 g/mol; about 450 g/mol; about 500 g/mol; about 550 g/mol; about 600 g/mol; about 650 g/mol; about 700 g/mol; about 750 g/mol; about 800 g/mol; about 850 g/mol; about 900 g/mol; about 950 g/mol; about 1000 g/mol; about 1050 g/mol; about 1150 g/mol; about 1200 g/mol; about 1250 g/mol; about 1300 g/mol; about 1350 g/mol; about 1400 g/mol; about 1450 g/mol; about 1500 g/mol; about 1550 g/mol; about 1600 g/mol; about 1650 g/mol; about 1700 g/mol; about 1750 g/mol; about 1800 g/mol; about 1850 g/mol; about 1900 g/mol; or about 1950 g/mol. In some embodiments, the compound comprising one or more carbonyl moiety is a liquid at about 20° C. or at about 25° C.

In some embodiments, the compound comprising one or more carbonyl moieties may be chemically attached to crosslinked beads or thin films. The beads or thin films are not particularly limited, but should be capable of withstanding the conditions under which the water is extracted. The beads or thin films should not disintegrate in the aqueous conditions under which the water is extracted, nor should they react with the gem diol formed during the conditions under which the water is extracted. Non limiting examples of beads or thin films capable of use in this disclosure include, polystyrenes and other solid-phase supports known in the art.

In some embodiments, the compound comprising one or more carbonyl moieties comprises one or more electron withdrawing moieties alpha to the carbonyl (e.g., 1, 2, 3 or 4). In some embodiments, the compound comprising one or more carbonyl moieties comprises two or more electron withdrawing moieties alpha or beta to the carbonyl (e.g., 2, 3, 4 or 5). Synthesis of this type of compound is within the purview of those skilled in the art [for example, F. A. Davis and P. V. N. Kasu, *Org. Prep. And Proc. Intern.*, 31(2): 125-143 (1999)]. Electron withdrawing moieties are known in the art, and may be used without limitation so long as they are stable in the conditions of the extraction process. Some non-limiting examples of electron withdrawing moieties include the group consisting of —Z or

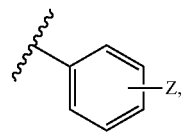

wherein Z is selected from —F, —Cl, —Br, —CF$_3$, —CF$_2$H, —CFH$_2$, —CN, NO$_2$, and —COO-alkyl. In some embodiments, more than one Z or other substitution on the phenyl moiety may be present.

In some embodiments, the compound comprising one or more carbonyl moieties is represented by formula (I):

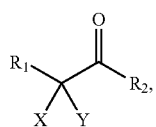

(I)

wherein X is an electron withdrawing moiety; Y is selected from the group consisting of an electron withdrawing moiety, H, optionally substituted alkyl, alkenyl, alkynyl, alkoxy, alkenoxy, alkynoxy, aryloxy, aralkyloxy, heterocyclyloxy, heterocyclylalkoxy, heteroalkyl, heteroalkenyl, and heteroalkynyl;

R$_1$ is selected from the group consisting of optionally substituted alkyl, alkenyl, alkynyl, alkoxy, alkenoxy, alkynoxy, aryloxy, aralkyloxy, heterocyclyloxy, heterocyclylalkoxy, heteroalkyl, heteroalkenyl, heteroalkynyl, and siloxanes;

R$_2$ is selected from the group consisting of H, optionally substituted alkyl, alkenyl, alkynyl, alkoxy, alkenoxy, alkynoxy, aryloxy, aralkyloxy, heterocyclyloxy, heterocyclylalkoxy, heteroalkyl, heteroalkenyl, heteroalkynyl, and siloxanes; with the proviso that when Y is H, then at least one of R$_1$ or R$_2$ is

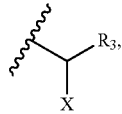

wherein R$_3$ is selected from the group consisting of optionally substituted alkyl, alkenyl, alkynyl, alkoxy, alkenoxy, alkynoxy, aryloxy, aralkyloxy, heterocyclyloxy, heterocyclylalkoxy, heteroalkyl, heteroalkenyl, heteroalkynyl, and siloxanes.

In some embodiments, X and Y of formula (I) together form a carbonyl or thioketone moiety.

In some embodiments, R$_1$ and R$_2$ are optionally substituted alkyl moieties. For example, methyl, ethyl, propyl or butyl. The alkyl moiety may optionally be substituted with one or more halo group, such as F.

The methods described herein may include a contacting step, for example contacting the aqueous solution described herein with a compound comprising one or more carbonyl moieties described herein. This method may be done on a commercial or industrial scale. Thus, in some embodiments, the method includes contacting an appropriate amount of aqueous solution, for example more than 5 L of aqueous solution, or in other embodiments for example, more than about 5, about 10, about 20, about 30, about 40, about 50, about 60, about 70, about 80, about 90, about 100, about 200, about 300, about 400, about 500, about 1,000, about 5,000, about 10,000 about 20,000, about 30,000, about 40,000, about 50,000, about 60,000, about 70,000, about 80,000, about 90,000, or about 100,000 L of aqueous solution, with the compound comprising one or more carbonyl moieties. In some embodiments, the molar ratio of water in the aqueous solution to carbonyl moieties capable of forming a gem diol under the extraction conditions may be at least 2:1 or about 5:1, about 10:1, about 50:1, about 100:1, about 150:1, about 200:1, or values therein between.

The contacting step is not particularly limited in that it can be conducted at, e.g., room temperature or another temperature below the boiling point of the aqueous solution and the compound comprising one or more carbonyl moieties.

Figure 3:
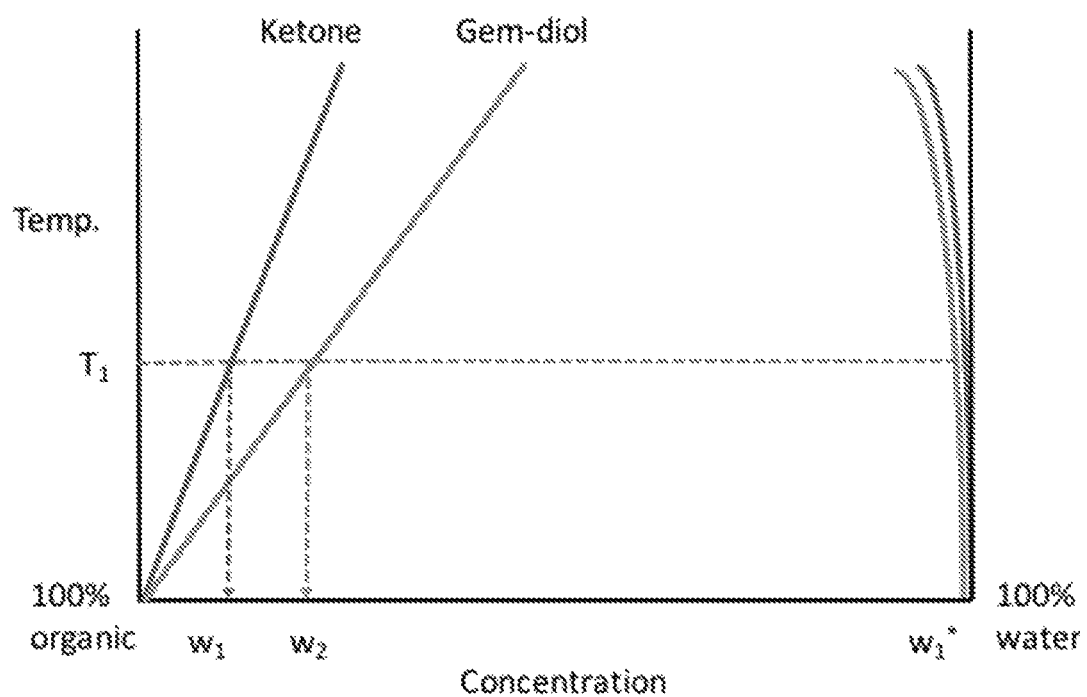
FIG. 3 shows target liquid-liquid phase behavior of ketone-water and gem-diol-water systems according to certain embodiments of the disclosure.

The methods described herein may also include a separating step, such as separating a composition comprising the hydrated compound from the aqueous solution. Thus, in some embodiments, the compound comprising one or more carbonyl moieties and/or the hydrated compound resulting therefrom has limited solubility in the aqueous solution (e.g., brine). In some embodiments, the compound comprising one or more carbonyl moieties and/or the hydrated compound resulting therefrom has an aqueous solubility at about 25° C. of less than about 1 wt. %, about 0.1 wt. %, about 0.01 wt. %, or about 0.001 wt. %. In some embodiments, the composition comprising the compound comprising one or more carbonyl moieties and/or the hydrated compound contains salt concentrations less than about 100 ppm (e.g., about 100, about 90, about 80, about 70, about 60, about 50, about 40, about 30, about 20, about 10, or about 5 or less ppm) when in contact with a 3% brine solution. For example, the compound comprising one or more carbonyl moieties and/or the hydrated compound may behave in a manner similar to the target liquid-liquid phase behavior of ketone-water and gem-diol-water systems according to FIG. 3. In FIG. 3, the x-axis is weight fraction water, where the origin represents 0% water and far right is 100% water; the y-axis is temperature. The two ketone branches of the phase boundary outline the 2-phase region, hence horizontal lines drawn on the graph show compositions of phases in equilibrium. At a temperature T$_1$, for example, there are two phases in equilibrium—an organic rich phase with some water (w$_1$) in equilibrium with an essentially pure water phase (w$_1$*, which is almost 100% water). When the ketone reacts with water to form the gem-diol, the phase boundary shifts to the right, meaning additional water enters the organic phase (point w$_2$). Upon reversal of the hydration reaction, the water held by the gem-diol is released, as well as the "extra" water (difference between w$_2$ and w$_1$).

The hydrated compound may be dehydrated once it has been removed from the aqueous solution environment. For example, some methods described herein may also include a step of reacting the hydrated compound to obtain water. This reaction may simply be allowing the hydrated compound to undergo reversible hydration. This step may require an outside stimulus, e.g., heat, to drive the reaction. In some embodiments, the composition comprising the hydrated compound is heated to e.g., about 30° C.; about 35° C.; about 40° C.; about 45° C.; about 50° C.; about 55° C.; about 60° C.; about 66° C.; about 70° C.; about 75° C.; about 80° C. or about 85° C. The water has limited solubility in the composition comprising the hydrated compound and may be isolated from this solution. The byproduct stream comprising the compound comprising one or more carbonyl moieties may then be recycled to undergo the contacting step once again.

As mentioned above, this method may be done on a commercial or industrial scale. FIG. 1 shows an embodiment of the process configuration for the disclosed subject matter on a commercial or industrial scale. In some embodiments, the aqueous solution (e.g., brine) may be fed continuously or in discrete segments into the first chamber charged with the compound comprising one or more carbonyl moieties. After the compound comprising one or more carbonyl moieties is allowed to become hydrates, it can be removed to a second chamber whereby the reversible hydration reaction is allowed to produce water and the compound comprising one or more carbonyl moieties. The water may then be collected, and the compound comprising one or more carbonyl moieties may be returned to the first chamber.

II. Compounds for Use in, e.g., Extracting Water

The present disclosure relates, in some embodiments, to compounds comprising one or more carbonyl moieties. For example, some embodiments include a compound represented by formula (I):

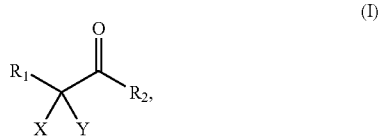

(I)

wherein X is an electron withdrawing moiety; Y is an electron withdrawing moiety or H; $R_1$ is selected from the group consisting of optionally substituted alkyl, alkenyl, alkynyl, alkoxy, alkenoxy, alkynoxy, aryloxy, aralkyloxy, heterocyclyloxy, heterocyclylalkoxy, heteroalkyl, heteroalkenyl, heteroalkynyl, and siloxanes; $R_2$ is selected from the group consisting of H, optionally substituted alkyl, alkenyl, alkynyl, alkoxy, alkenoxy, alkynoxy, aryloxy, aralkyloxy, heterocyclyloxy, heterocyclylalkoxy, heteroalkyl, heteroalkenyl, heteroalkynyl, and siloxanes; with the proviso that when Y is H, then at least one of $R_1$ or $R_2$ is represented by (A)

(A)

wherein $R_3$ is selected from the group consisting of optionally substituted alkyl, alkenyl, alkynyl, alkoxy, alkenoxy, alkynoxy, aryloxy, aralkyloxy, heterocyclyloxy, heterocyclylalkoxy, heteroalkyl, heteroalkenyl, heteroalkynyl, and siloxanes. In some embodiments, X and Y of formula (I) together form a carbonyl or thioketone moiety. In some embodiments, $R_1$ and $R_2$ are optionally substituted alkyl moieties such as, for example, methyl, ethyl, propyl or butyl. The alkyl moiety may optionally be substituted with one or more halo group, such as F.

Other compounds of the present disclosure include compounds comprising one or more gem diol moiety. For example, some embodiments include a compound represented by formula(II):

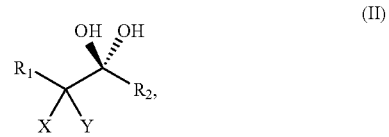

(II)

wherein X is an electron withdrawing moiety; Y is an electron withdrawing moiety or H; $R_1$ is selected from the group consisting of optionally substituted alkyl, alkenyl, alkynyl, alkoxy, alkenoxy, alkynoxy, aryloxy, aralkyloxy, heterocyclyloxy, heterocyclylalkoxy, heteroalkyl, heteroalkenyl, heteroalkynyl, and siloxanes; $R_2$ is selected from H, optionally substituted alkyl, alkenyl, alkynyl, alkoxy, alkenoxy, alkynoxy, aryloxy, aralkyloxy, heterocyclyloxy, heterocyclylalkoxy, heteroalkyl, heteroalkenyl, heteroalkyny, and siloxanes; with the proviso that when Y is H, then at least one of $R_1$ or $R_2$ is

wherein $R_3$ is selected from the group consisting of optionally substituted alkyl, alkenyl, alkynyl, alkoxy, alkenoxy, alkynoxy, aryloxy, aralkyloxy, heterocyclyloxy, heterocyclylalkoxy, heteroalkyl, heteroalkenyl, heteroalkynyl, and siloxanes. In some embodiments, X and Y of formula (II) together for a carbonyl or thioketone moiety. In some embodiments, $R_1$ and $R_2$ are optionally substituted alkyl moieties such as, for example, methyl, ethyl, propyl or butyl. The alkyl moiety may optionally be substituted with one or more halo group, such as F.

In some embodiments, the variables in formula (II) can be the same as listed for formula (I).

III. Definitions

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, the term "electron withdrawing moiety" refers to a chemical moiety that has a greater electron withdrawing effect than hydrogen. A variety of electron-withdrawing moieties are known and include, by way of example, halogens (e.g., fluoro, chloro, bromo, and iodo groups), $NO_2$, $NR_3^+$, CN, COOH(R), fluorinated alkyls (e.g., $CF_2H$, $CFH_2$, $CF_3$), and the like. The electron-withdrawing moiety may also comprise a spacer portion that, such as an aromatic or conjugated moiety that allows for the electron-withdrawing portion of the moiety to have an electronic effect on the carbonyl, for example, a phenylene spacer portion. In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocycle, and heteroaryl groups also include rings and fused ring systems in which a bond to a hydrogen atom is replaced with a bond to a carbon atom. Therefore, substituted cycloalkyl, aryl, heterocycle, and heteroaryl groups may also be substituted with substituted or unsubstituted alkyl, alkenyl, and alkynyl groups as defined below.

Alkyl groups include straight chain and branched alkyl groups having from 1 to about 20 carbon atoms, and typically from 1 to 12 carbons or, in some embodiments, from 1 to 8, 1 to 6, or 1 to 4 carbon atoms. Alkyl groups further include cycloalkyl groups as defined below. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above. In certain embodiments, an alkyl comprises of a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In certain embodiments, an alkyl comprises one to six carbon atoms (e.g., $C_1$-$C_6$ alkyl). In certain embodiments, an alkyl comprises two to eight carbon atoms (e.g., $C_2$-$C_8$ alkyl). In certain embodiments, an alkyl comprises two to six carbon atoms (e.g., $C_2$-$C_6$ alkyl). In certain embodiments, an alkyl comprises one to three carbon atoms (e.g., $C_1$-$C_3$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl).

Alkenyl groups include straight and branched chain and cycloalkyl groups as defined above, except that at least one double bond exists between two carbon atoms. Thus, alkenyl groups have from 2 to about 20 carbon atoms, and typically from 2 to 12 carbons or, in some embodiments, from 2 to 8, 2 to 6, or 2 to 4 carbon atoms. In some embodiments, alkenyl groups include cycloalkenyl groups having from 4 to 20 carbon atoms, 5 to 20 carbon atoms, 5 to 10 carbon atoms, or even 5, 6, 7, or 8 carbon atoms. Examples include, but are not limited to vinyl, allyl, —CH=CH($CH_3$), —CH=C($CH_3$)$_2$, —C($CH_3$)=$CH_2$, —C($CH_3$)=CH($CH_3$), —C($CH_2CH_3$)=$CH_2$, cyclohexenyl, cyclopentenyl, cyclohexadienyl, butadienyl, pentadienyl, and hexadienyl, among others. Representative substituted alkenyl groups may be mono-substituted or substituted more than once, such as, but not limited to, mono-, di- or tri-substituted with substituents such as those listed above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8, 2 to 6, or 2 to 4 carbon atoms. Examples include, but are not limited to —C≡CH, —C≡C ($CH_3$), —C≡C($CH_2CH_3$), —$CH_2$C≡CH, —$CH_2$C≡C($CH_3$), and —$CH_2$C≡C($CH_2CH_3$), among others. Representative substituted alkynyl groups may be mono-substituted or substituted more than once, such as, but not limited to, mono-, di- or tri-substituted with substituents such as those listed above.

Heteroalkyl, heteroalkenyl, and heteroalkynyl refer to alkyl, alkenyl, and alkynyl referred to above where at least one carbon is replaced by a heteroatom, such as O, S, Si, and N. The heteroatom may itself be substituted depending on the valence. For example, the N may be an amine; the S may be S, SO, $SO_2$, SR, et cetera, where R is a substitution such as alkyl; Si may be $SiO_2$ or $SR_2$, for example. Some embodiments, include siloxane substitution where two adjacent carbons are replaced by $SR_2$ and O, respectively.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include mono-, bicyclic and polycyclic ring systems, such as, for example bridged cycloalkyl groups as described below, and fused rings, such as, but not limited to, decalinyl, and the like. In some embodiments, polycyclic cycloalkyl groups have three rings. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or or 2,6-disubstituted cyclohexyl groups, which may be substituted with substituents such as those listed above.

Bridged cycloalkyl groups are cycloalkyl groups in which two or more hydrogen atoms are replaced by an alkylene bridge, wherein the bridge can contain 2 to 6 carbon atoms if two hydrogen atoms are located on the same carbon atom, or 1 to 5 carbon atoms, if the two hydrogen atoms are located on adjacent carbon atoms, or 2 to 4 carbon atoms if the two hydrogen atoms are located on carbon atoms separated by 1 or 2 carbon atoms. Bridged cycloalkyl groups can be bicyclic, such as, for example bicyclo[2.1.1]hexane, or tricyclic, such as, for example, adamantyl. Representative bridged cycloalkyl groups include bicyclo[2.1.1]hexyl, bicyclo[2.2.1]heptyl, bicyclo[3.2.1]octyl, bicyclo[2.2.2]octyl, bicyclo[3.2.2]nonyl, bicyclo[3.3.1]nonyl, bicyclo[3.3.2]decanyl, adamantyl, noradamantyl, bornyl, or norbornyl groups. Substituted bridged cycloalkyl groups may be substituted one or more times with non-hydrogen and non-carbon groups as defined above. Representative substituted bridged cycloalkyl groups may be mono-substituted or substituted more than once, such as, but not limited to, mono-, di- or tri-substituted adamantyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 20 carbon atoms, 4 to 16 carbon atoms, and typically 4 to 10 carbon atoms. Substituted cycloalkylalkyl groups may be substituted at the alkyl, the cycloalkyl, or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Cycloalkenylalkyl groups are alkyl groups as defined above in which a hydrogen or carbon bond of the alkyl group is replaced with a bond to a cycloalkenyl group as defined above. Substituted cycloalkylalkenyl groups may be substituted at the alkyl, the cycloalkenyl, or both the alkyl and cycloalkenyl portions of the group. Representative substituted cycloalkenylalkyl groups may be substituted one or more times with substituents such as those listed above.

Aryl groups are cyclic aromatic hydrocarbons that do not contain heteroatoms. Aryl groups include monocyclic, bicyclic, and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 20 carbon atoms, 7 to 14 carbon atoms or 7 to 10 carbon atoms. Substituted aralkyl groups may be substituted at the alkyl, the aryl, or both the alkyl and aryl portions of the group. Representative aralkyl groups include but are not limited to benzyl and phenethyl groups and fused (cycloalkylaryl)alkyl groups such as 4-ethyl-indanyl. Representative substituted aralkyl groups may be substituted one or more times with substituents such as those listed above.

Heterocycle groups include aromatic (also referred to as heteroaryl) and non-aromatic ring compounds containing 3 or more ring members, of which one or more is a heteroatom such as, but not limited to, N, O, and S. In some embodiments, heterocycle groups include 3 to 20 ring members, whereas other such groups have 3 to 6, 3 to 10, 3 to 12, or 3 to 15 ring members. Heterocycle groups encompass unsaturated, partially saturated and saturated ring systems, such as, for example, imidazolyl, imidazolinyl and imidazolidinyl groups. The phrase "heterocycle group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocycle groups that have other groups, such as alkyl, oxo or halo groups, bonded to one of the ring members. Rather, these are referred to as "substituted heterocycle groups". Heterocycle groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocycle groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridyl, pyridazinyl, pyrimidinyl, pyrazinyl, thiophenyl, benzothiophenyl, furanyl, benzofuranyl, indolyl, azaindolyl (pyrrolopyridyl), indazolyl, benzimidazolyl, imidazopyridyl (azabenzimidazolyl), pyrazolopyridyl, triazolopyridyl, benzotriazolyl, benzoxazolyl, benzothiazolyl, benzothiadiazolyl, imidazopyridyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups. Although the phrase "heteroaryl groups" includes fused ring compounds such as indolyl and 2,3-dihydro indolyl, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocycle group as defined above. Substituted heterocyclylalkyl groups may be substituted at the alkyl, the heterocycle or both the alkyl and heterocycle portions of the group. Representative heterocycle alkyl groups include, but are not limited to, 4-ethylmorpholinyl, 4-propylmorpholinyl, furan-2-yl methyl, furan-3-yl methyl, pyridine-3-yl methyl, tetrahydrofuran-2-yl ethyl, and indol-2-yl propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "amine" (or "amino") as used herein refers to —NHR and —NRR groups, wherein R is independently hydrogen, or a substituted or unsubstituted alkyl, alkenyl, alkynyl, cycloalkyl, aryl, aralkyl, heterocyclylalkyl or heterocycle group as defined herein. In some embodiments, the amine is NH$_2$, methylamino, dimethylamino, ethylamino, diethylamino, propylamino, isopropylamino, phenylamino, or benzylamino.

The term "amide" refers to a —NR'R''C(O)— group wherein R' and R'' each independently refer to a hydrogen, (C$_1$-C$_8$)alkyl, or (C$_3$-C$_6$)aryl.

The term "nitrile" or "cyano" can be used interchangeably and refer to a —CN group which is bound to a carbon atom of a heteroaryl ring, aryl ring and a heterocycloalkyl ring.

The term "siloxane" includes moieties with at least one SiR$_2$O moiety. For example, in some embodiments, they may include the following repeat unit.

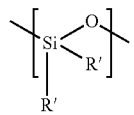

where R' is independently H, optionally substituted alkyl, alkenyl, alkynyl, alkoxy, alkenoxy, alkynoxy, aryloxy, aralkyloxy, heterocyclyloxy, heterocyclylalkoxy, heteroalkyl, heteroalkenyl, heteroalkynyl, as defined elsewhere herein.

The terms "optional" or "optionally" mean that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

The following examples are given to illustrate the present invention. It should be understood, however, that the invention is not to be limited to the specific conditions or details described in these examples.

EXAMPLES

Example 1: Exemplary Calculation

Using first principles calculations, one can calculate the Gibbs free energy change of a reaction (ΔG) and then calculate the equilibrium constant of a reaction as $K_{eq}=e^{-\Delta G/RT}$. This approach was followed using the M06-2X level of theory to calculate the equilibrium constant of octanone hydration with different functional groups in positions neighboring to the ketone group. The calculated $K_{eq}$ values can be further scaled based on experimental hydration reaction data of known molecules to derive the final predicted values. The following table demonstrates an effect on the predicted equilibrium constant of ketone hydration based upon three different positions of substitution.

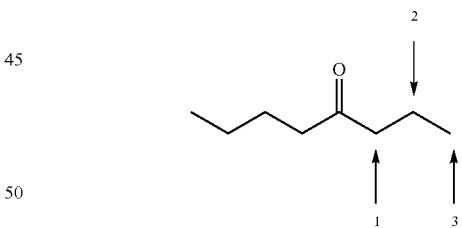

| Functional Group: | Predicted K$_{eq}$ | | | Methyl-Ester |
|---|---|---|---|---|
| | F | CN | Cl | |
| No Additions | 0.04 | 0.04 | 0.04 | 0.04 |
| 1 | 15.07 | 4.66 | 1.64 | 1.81 |
| 2 | 6.30 | 0.71 | 0.21 | 1.33 |
| 3 | 0.28 | 0.57 | 0.09 | 0.03 |

A thermodynamic model created specifically to examine salt-water-organic systems [Zuend et al., *Atmos. Chem. Phys.*, 8: 4559-4593 (2008); Zuend et al., *Atmos. Chem.*

*Phys.,* 11: 9155-9206 (2011)] was employed to examine target liquid-liquid phase behavior of the ketone-water and gem-diol-water systems. The model allows one to build the organic component as an assembly of functional groups (a so-called group contribution approach), which then enabled examination of the impact of the structure of the extractant on phase behavior. The model was applied to a simple system comprising an alkyl (inactivated) ketone, water, and sodium chloride (3% in the water). The initial model results showed that indeed, even a relatively small carbonyl ($C_8$-functional ketone) exhibits the desired asymmetric phase diagram with 5-7% water influx into the organic phase, less than 0.5% organic in the aqueous phase, and that salt migration into the organic phase was less than 25 ppm.

The disparity in size between the extractant and water appeared to create the needed asymmetric phase envelope as shown in FIG. 4; it is also useful in ensuring that the extractant is non-volatile. The models used were embedded within commercially-available ASPEN process simulator software to predict boiling points—values greater than 150° C. are desirable and entirely tractable.

Example 2

A. General Considerations and Synthesis

Water was HPLC grade, while dimethyl sulfoxide (DMSO) and d6-DMSO were ≥99.9% pure. Examples (2-3 to 2-11) were available commercially and used without further purification. Synthesis of 3-methyl-3-nitrobutan-2-one (Structure 1) and 2,2-difluoro-1-phenyl-1-propanone (Example 2-2) are described below. Mass measurements were made on an analytical balance with ±0.1 mg precision. Volumetric flasks were of Class A precision. NMR tubes were rated for field strengths of ≤500 MHz. All NMR measurements were made on a Bruker Avance III 400 MHz NMR either at ambient temperature or with variable temperature control. NMR tubes were thoroughly rinsed with acetone multiple on a vacuum NMR tube washer and stored in an 80-100° C. oven between uses.

B. Synthesis of 3-methyl-3-nitrobutan-2-one 3-methyl-3-nitrobutan-2-one was prepared by a method adapted from the literature [Zhang et al., *Org. Lett.* 19: 1124-1127 (2017)]. A magnetic stir bar, 3-methyl-2-butanone (0.874 g, 10.1 mmol) dissolved in 1,2-dichloroethane (15 mL), copper(II) acetate (0.370 g, 0.2 equiv.), and ammonium cerium(IV) nitrate (11.118 g, 2 equiv.) were successively added to a flame-dried 250 mL Schlenk tube under Ar. After the addition of each reagent the flask was cycled between vacuum and Ar three times to remove any residual oxygen. The reaction was stirred for 24 hours at 80° C.

The reaction mixture was filtered to remove the salts. Solvent was removed by vacuum and the crude material was purified by silica flash chromatography (hexanes →4% acetone in hexanes). Fractions containing product were combined and solvent removed under vacuum leaving a yellow solid (0.1003 g, 7.5% yield). 1HNMR (400 MHz, CDCl3)δ 2.24 (s, 3H), 1.74 (s, 6H). 13CNMR (100 MHz, CDCl3)δ 199.6, 94.1, 24.3, 24.0, and 23.11. HRMS m/z calculated for C5H10O3 [M+H]+: 132.06552; found 132.06684.

C. Synthesis of 2,2-difluoro-1-phenyl-1-propanone 2,2-difluoro-1-phenyl-1-propanone was prepared according to the literature [Kosobokov et al., *Org. Lett.*, 17:760-763 (2015)]. In a 3-arm 50 mL round bottom flask with a magnetic stir bar, acetophenone (1.1999 g, 10 mmol) and triethyl amine (2 mL, 14 mmol) were dissolved in anhydrous dioxane (20 mL) under Ar. Residual oxygen was removed by the freeze-pump thaw method. $Me_3SiOTf$ (1.8 mL, 12 mmol) was added while the solution was cooled at 0° C. with an ice-water bath. The ice bath was removed and the reaction was stirred for 40 min. at room temperature. Hexamethylphosphoramide (5.2 mL, 30 mmol) and $Me_3SiCF_2Br$ (5.2 mL, 35 mmol) was added over a 10° C. ice bath. Reaction color changed from clear to cloudy yellow. Reaction was stirred at room temperature for approximately 20 hours.

Volatile components were removed by placing the reaction under vacuum for approximately 3 hours. The reaction was transferred to a 1000 mL round bottom flask and treated with a solution of 33% v/v HBr in AcOH (20 mL, 110 mmol) and water (2 mL, 110 equiv). The flask was flushed with Ar the sealed and heated at 80° C. for 1 hour.

After cooling to room temperature, the reaction was quenched with an aqueous solution of saturated $Na_2CO_3$ (100 mL) and water (100 mL). The aqueous phase was extracted with 3×60 mL of pentane/$Et_2O$ (v/v, 1:1). The combined organic layers were dried with sodium sulfate and filtered. Solvent was removed under rotary evaporation and the product was purified by silica flash chromatography (15/1, pentane/$Et_2O$). Fractions containing product were combined and solvent removed under vacuum (0.8240 g, 48% yield); NMR and HRMS were consistent with the published literature.

D. Methods for Equilibrium Measurements

Ketone hydration to diol equilibrium constants (KH) and thermodynamic parameters for Example compounds were measured by NMR by adapting techniques from the literature [Bushman et al., *Berichte der Bunsengesellschaft für physikalische Chemie,* 84: 41-44 (1980); Greenzaid et al., *J. Amer. Chem. Soc.* 89: 749-756 (1967); and R. Stewart and J. D. Van Dyke, *Can. J. Chem.* 50: 1992-1999 (1972)] using either Technique 1 (IIa) or Technique 2 (IIb), further deviations to the general methods are noted with those Examples. $D_2O$ concentration was minimized to reduce the isotope effect (~20% according to Bushman 1980).

The conversion from ketone to diol results in an upfield change in nuclear chemical shift. This change in nuclear resonance frequency can then be used to distinguish between ketone and diol peaks in the NMR spectrum. Since area integration of NMR peaks is directly related to the number of atoms resonating at that frequency, the area ratio between diol and ketone peaks can be used to calculate equilibrium constants. Assuming water is in high excess relative to the ketone its activity can be treated as unity resulting in the KH being only dependent on the relative peak integration ratio of diol/ketone:

$$K_H = \frac{\text{Integration of Diol Proton Peaks}}{\text{Integration of Ketone Proton Peaks}}.$$

In many Examples, only a single resonance for each species was available for to determine the diol/ketone ratio. Where available equilibrium constants were calculated by averaging multiple resonance together normalized by number of hydrogens associated with each of them.

Due to the insolubility of some ketones in water, DMSO was used as a co-solvent at 50% by mole. Equilibrium constants obtained with DMSO as a co-solvent are only apparent constants (KH,app) since this alters the activities of the compounds relative to a pure water solvent. Example 2-11 demonstrates that KH,app<KH, consistent with previous findings [R. Stewart and J. D. Van Dyke, *Can. J. Chem.* 50: 1992-1999 (1972)].

For a select set of compounds a series of variable temperature NMR measurements (IIB: Technique 2) were made to extract reaction standard enthalpy($\Delta H°$) and entropy ($\Delta S°$) contributions to free energy of hydration)($\Delta G°$). Equilibrium constants versus temperature data were fit to the van't Hoff equation to determine $\Delta H°$, $\Delta S°$, and $\Delta G°$; changes in heat capacity were assumed to be negligible:

$$K_H = e^{\frac{-1}{R}\left(\frac{\Delta H°}{T} - \Delta S°\right)} \text{ and } \Delta G° = \Delta H° - (298K)\Delta S°.$$

E. TECHNIQUE 1: Room Temperature NMR Measurements

In a volumetric flask, ketones were dissolved to a concentration of approximately 0.5 M in 50 mol % $d^6$-DMSO/$H_2O$. Solutions were left to equilibrate overnight then transferred to an NMR tube for analysis. Solutions were measured by $^1H$ NMR at (400 MHz) or $^{19}F$ NMR (376 MHz) at ambient temperature (20±1° C.).

F. TECHNIQUE 2: Variable Temperature NMR Measurements

In a volumetric flask (1.00, 2.00, or 10.00 mL) ketones were dissolved to a concentration of approximately 0.5 M in solvents composed of either $D_2O/H_2O$ (5/95, v/v; method 2a) or $d^6$-DMSO/DMSO/$H_2O$ (10/40/50 by moles; method 2b). The solution was left to equilibrate at room temperature overnight then transferred to a standard NMR tube.

A series of 1H NMR (400 MHz) measurements were made with variable temperature control (0.1° C. precision) ranging from 25-65° C., typically in 10° C. increments. At each increment once the temperature had stabilized to within ±0.2° C. of the goal, samples were equilibrated for 5 minutes prior to the measurement.

G. Example Structures and Thermodynamics

Examples 2-1 to 2-5

Equilibrium constants of Examples 2-1 to 2-5 were determined by Technique 1; structures and results are listed in Table 1. Example 2-1 was measured at a concentration of only 23 mM due to the small quantities at hand and its low solubility in water. This should not affect the measured hydration equilibrium greatly though since water is in such high excess. From Examples 2-2 to 2-5, the tunability of the hydration constant by altering the substituent on the benzyl ring is readily apparent.

TABLE 1

| Example | Structure | Solvent | $K_{H,app}$ at 20 ± ° C. |
|---|---|---|---|
| 2-1 | | $D_2O/H_2O$ (5/95, v/v) | 0.22 |
| 2-2 | 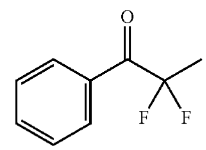 | $d^6$-DMSO/$H_2O$ (1/1, mol/mol) | 2.8 ($^1H$), 3.3 ($^{19}F$) |
| 2-3 | 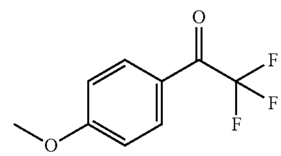 | $d^6$-DMSO/$H_2O$ (1/1, mol/mol) | 21 ($^1H$), 23 ($^{19}F$) |
| 2-5 | 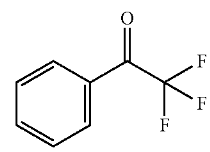 [SMILES: O=C(c1ccccc1)C(F)(F)F] | $d^6$-DMSO/$H_2O$ (1/1, mol/mol) | 370 ($^{19}F$) |
| 2-4 | 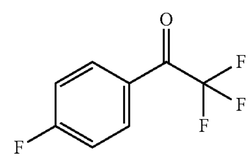 [SMILES: O=C(c1ccc(F)cc1)C(F)(F)F] | $d^6$-DMSO/$H_2O$ (1/1, mol/mol) | 500 ($^{19}F$) |

Examples 2-6 to 2-11

The effects of temperature on KH for Examples 2-6 to 2-11 were measured using Technique 2 and are listed in Table 2. The van't Hoff equation was then fit to a plot of KH vs. temperature; energy standard deviation were calculated from the fit of the equation to the raw data.

Examples 2-6 and 2-11 were prepared using variations to the standard procedure. Example 2-6 was prepared with a concentration of 50 mM, so that it was soluble in water. For Example 2-11, a small amount of enol was also observed (about 0.08 relative to ketone). To account for this, we calculated KH for Example 2-11 as diol/(ketone+enol), assuming enol formation from the ketone is reversible.

TABLE 2

| Example | Structure | Solvent | $K_H$ at 25° C. | $\Delta H°$, kJ/mol | $-T\Delta S°$, kJ/mol | $\Delta G°$, kJ/mol |
|---|---|---|---|---|---|---|
| 2-6 | 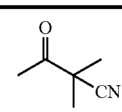 | $D_2O/H_2O$ (5/95, v/v) | 0.063 | −24.5 ± 1.5 | 31.3 ± 1.4 | 6.8 ± 2 |
| 2-7 | 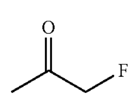 | $D_2O/H_2O$ (5/95, v/v) | 0.15 | −20.6 ± 0.3 | 25.3 ± 0.2 | 4.7 ± 0.3 |
| 2-8 | 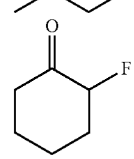 | DMSO/$H_2O$ (1/1, mol/mol) | 0.52$^a$ | −22.4 ± 0.4 | 26.4 ± 0.6 | 4 ± 0.7 |
| 2-9 | 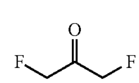 | $D_2O/H_2O$ (5/95, v/v) | 27 | −31.4 ± 0.7 | 23.3 ± 0.7 | −8.1 ± 1 |

TABLE 2-continued

| Example | Structure | Solvent | $K_H$ at 25° C. | ΔH °, kJ/mol | −TΔS °, kJ/mol | ΔG °, kJ/mol |
|---|---|---|---|---|---|---|
| 2-10 | (structure) | D$_2$O/H$_2$O (5/95, v/v) | 2.5 | −25 ± 1.5 | 22.8 ± 1.5 | −2.2 ± 1.5 |
| 2-11 | (structure) | D$_2$O/H$_2$O (5/95, v/v) | 1.5 | −22.9 ± 0.5 | 21.8 ± 0.5 | −1.1 ± 0.5 |
|  |  | DMSO/ H$_2$O (1/1, mol/mol) | 0.45[a] | −24 ± 1 | 26 ± 1 | 2 ± 1 |

[a]Equilibrium constant represents $K_{H, app}$ due to the difference in solvent.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A method for extracting water from an aqueous solution, comprising:
   (a) contacting the aqueous solution with a compound comprising one or more carbonyl moieties and one or more electron withdrawing moieties alpha to the carbonyl, having an equilibrium constant for a hydration of the carbonyl moiety of at least about 0.5;
   (b) separating a composition comprising the hydrated compound from the aqueous solution; and
   (c) reacting the hydrated compound to obtain water.

2. The method of claim 1, wherein the aqueous solution comprises a salt.

3. The method of claim 1, wherein the aqueous solution is brine.

4. The method of claim 1, wherein the compound comprising one or more carbonyl moieties comprises two or more electron withdrawing moieties alpha or beta to the carbonyl.

5. The method of claim 1, wherein the electron withdrawing moiety is independently in each instance selected from the group consisting of —Z or

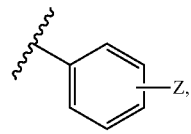

and wherein Z is selected from —F, —Cl, —CN, NO$_2$, carbonyl, and —COO-alkyl.

6. The method of claim 1, wherein the compound comprising one or more carbonyl moieties has a boiling point of greater than about 100° C.

7. The method of claim 1, wherein reacting the hydrated compound to obtain water comprises heating the hydrated compound to a temperature of about 40° C. to about 100° C.

8. The method of claim 1, wherein the compound comprising one or more carbonyl moieties has a molecular weight of about 150 g/mol to about 400 g/mol.

9. The method of claim 1, wherein the compound comprising one or more carbonyl moieties is chemically attached to crosslinked beads or a thin film.

10. The method of claim 1, wherein the compound comprising one or more carbonyl moieties is represented by formula (I):

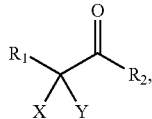

(I)

wherein:
X is an electron withdrawing moiety;
Y is selected from the group consisting of an electron withdrawing moiety, H, optionally substituted alkyl, optionally substituted alkenyl, optionally substituted alkynyl, optionally substituted alkoxy, optionally substituted alkenoxy, optionally substituted alkynoxy, optionally substituted aryloxy, optionally substituted aralkyloxy, optionally substituted heterocyclyloxy, optionally substituted heterocyclylalkoxy, optionally substituted heteroalkyl, optionally substituted heteroalkenyl, optionally substituted heteroalkynyl, and optionally substituted siloxanes; and X and Y of formula (I) together form a carbonyl or a thioketone moiety;
$R_1$ is selected from the group consisting of optionally substituted alkyl, optionally substituted alkenyl, optionally substituted alkynyl, optionally substituted alkoxy, optionally substituted alkenoxy, optionally substituted alkynoxy, optionally substituted aryloxy, optionally substituted aralkyloxy, optionally substituted heterocyclyloxy, optionally substituted heterocyclylalkoxy, optionally substituted heteroalkyl, optionally substituted heteroalkenyl, optionally substituted heteroalkynyl, and optionally substituted siloxanes;
$R_2$ is selected from the group consisting of H, optionally substituted alkyl, optionally substituted alkenyl, optionally substituted alkynyl, optionally substituted alkoxy, optionally substituted alkenoxy, optionally substituted alkynoxy, optionally substituted aryloxy, optionally substituted aralkyloxy, optionally substituted heterocyclyloxy, optionally substituted heterocyclylalkoxy, optionally substituted heteroalkyl, optionally substituted heteroalkenyl, optionally substituted heteroalkynyl, and optionally substituted siloxanes;
with the proviso that when Y is H, then at least one of $R_1$ or $R_2$ is

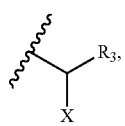

and
wherein $R_3$ is selected from the group consisting of optionally substituted alkyl, optionally substituted alkenyl, optionally substituted alkynyl, optionally substituted alkoxy, optionally substituted alkenoxy, optionally substituted alkynoxy, optionally substituted aryloxy, optionally substituted aralkyloxy, optionally substituted heterocyclyloxy, optionally substituted heterocyclylalkoxy, optionally substituted heteroalkyl, optionally substituted heteroalkenyl, optionally substituted heteroalkynyl, and optionally substituted siloxanes.

11. The method of claim 10, wherein the compound of formula (I) has a molecular weight of at least about 150 g/mol to about 400 g/mol.

12. The method of claim 10, wherein the electron withdrawing moiety is independently in each instance selected from the group consisting of Z or

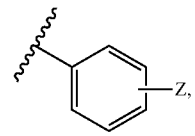

wherein Z is selected from —F, —Cl, —Br, —$CF_3$, —$CF_2H$, —$CFH_2$, —CN, $NO_2$, and —COO-alkyl.

13. The method of claim 1, wherein the compound has a theoretical equilibrium constant for a hydration of the carbonyl moiety of at least about 1 as calculated by (1) using first principles to calculate Gibbs free energy change of a reaction (ΔG) and then (2) calculating the equilibrium constant of a reaction as $K_{eq} = e^{-\Delta G/RT}$ using M06-2X level of theory.

14. The method of claim 10, wherein the one or more electron withdrawing moieties is —Z, wherein Z is selected from —F, —Cl, —Br, —$CF_3$, —$CF_2H$, —$CFH_2$, —CN, $NO_2$, and —COO-alkyl.

15. The method of claim 10, wherein the compound has an equilibrium constant for a hydration of the carbonyl moiety of at least about 1.

16. The method of claim 10, wherein Y is H.

17. The method of claim 10, wherein $R_1$ is represented by

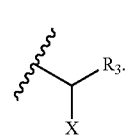

(A)

18. The method of claim 10, wherein $R_2$ is represented by

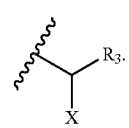

(A)

19. The method of claim 1, wherein the method is conducted on at least a 100 L of aqueous solution scale.

* * * * *